United States Patent
Jang et al.

(10) Patent No.: US 10,074,809 B2
(45) Date of Patent: Sep. 11, 2018

(54) ELECTRON TRANSPORT MATERIALS WITH SELECTED DIPOLE MOMENTS

(71) Applicant: LG CHEM, LTD., Seoul (KR)

(72) Inventors: Boonjae Jang, Daejeon (KR); Jungl Jang, Daejeon (KR); Seong So Kim, Daejeon (KR); Dong Hoon Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 7 days.

(21) Appl. No.: 15/509,178

(22) PCT Filed: Oct. 27, 2015

(86) PCT No.: PCT/KR2015/011393
§ 371 (c)(1),
(2) Date: Mar. 6, 2017

(87) PCT Pub. No.: WO2016/068585
PCT Pub. Date: May 6, 2016

(65) Prior Publication Data
US 2017/0279055 A1    Sep. 28, 2017

(30) Foreign Application Priority Data
Oct. 27, 2014  (KR) .......................... 10-2014-0146402

(51) Int. Cl.
*H01L 51/00* (2006.01)
*C07D 401/10* (2006.01)
(Continued)

(52) U.S. Cl.
CPC ........ *H01L 51/0062* (2013.01); *C07C 255/50* (2013.01); *C07D 209/86* (2013.01);
(Continued)

(58) Field of Classification Search
None
See application file for complete search history.

(56) References Cited

U.S. PATENT DOCUMENTS

| 7,902,742 B2 | 3/2011 | Suzuki et al. |
| 8,057,917 B2 | 11/2011 | Begley et al. |

(Continued)

FOREIGN PATENT DOCUMENTS

| CN | 104538554 A | 4/2015 |
| EP | 1575339 A1 | 9/2005 |

(Continued)

OTHER PUBLICATIONS

C. W. Tang et al., "Organic electroluminescent diodes", Applied Physics Letters 51 (12), Sep. 21, 1987, pp. 913-915.
(Continued)

*Primary Examiner* — Joseph Schoenholtz
(74) *Attorney, Agent, or Firm* — Dentons US LLP

(57) ABSTRACT

An exemplary embodiment of the present specification provides an organic electroluminescence device including: an anode; a cathode; a light emitting layer provided between the anode and the cathode; and an electron transporting layer provided between the cathode and the light emitting layer, in which the electron transporting layer includes a first electron transporting material and a second electron transporting material, the first electron transporting material is an organic material including a monocyclic or polycyclic ring which includes an N-containing six-membered ring, the second electron transporting material is an organic material including a five-membered hetero ring which includes at least one heteroatom of N, O, and S, or a cyano group, and a dipole moment of the second electron transporting material is larger than a dipole moment of the first electron transporting material.

13 Claims, 1 Drawing Sheet

(51) Int. Cl.

| | |
|---|---|
| *C07C 255/50* | (2006.01) |
| *C07D 209/86* | (2006.01) |
| *C07D 235/02* | (2006.01) |
| *C07D 235/08* | (2006.01) |
| *C07D 239/26* | (2006.01) |
| *C07D 251/24* | (2006.01) |
| *C07D 263/57* | (2006.01) |
| *C07D 277/66* | (2006.01) |
| *C09K 11/02* | (2006.01) |
| *C07D 403/10* | (2006.01) |
| *C07D 403/14* | (2006.01) |
| *H01L 51/50* | (2006.01) |
| *C09K 11/06* | (2006.01) |
| *H01L 51/52* | (2006.01) |

(52) U.S. Cl.
CPC ......... *C07D 235/02* (2013.01); *C07D 235/08* (2013.01); *C07D 239/26* (2013.01); *C07D 251/24* (2013.01); *C07D 263/57* (2013.01); *C07D 277/66* (2013.01); *C07D 401/10* (2013.01); *C07D 403/10* (2013.01); *C07D 403/14* (2013.01); *C09K 11/025* (2013.01); *C09K 11/06* (2013.01); *H01L 51/006* (2013.01); *H01L 51/0052* (2013.01); *H01L 51/0056* (2013.01); *H01L 51/0058* (2013.01); *H01L 51/0061* (2013.01); *H01L 51/0067* (2013.01); *H01L 51/0071* (2013.01); *H01L 51/0072* (2013.01); *H01L 51/50* (2013.01); *C09K 2211/1007* (2013.01); *C09K 2211/1011* (2013.01); *C09K 2211/1014* (2013.01); *H01L 51/0054* (2013.01); *H01L 51/5012* (2013.01); *H01L 51/5072* (2013.01); *H01L 51/5092* (2013.01); *H01L 51/5206* (2013.01); *H01L 51/5221* (2013.01)

(56) References Cited

U.S. PATENT DOCUMENTS

| | | | |
|---|---|---|---|
| 8,587,193 | B2 | 11/2013 | Suzuki et al. |
| 2012/0256172 | A1 | 10/2012 | Ito et al. |
| 2016/0197289 | A1* | 7/2016 | Sado .................... C07D 405/14 257/40 |
| 2018/0114920 | A1* | 4/2018 | Frey .................... H01L 51/0067 |

FOREIGN PATENT DOCUMENTS

| | | | |
|---|---|---|---|
| EP | 3208861 A1 * | 8/2017 | |
| KR | 10-2013-0060953 A | 6/2013 | |
| KR | 1020130060953 A | 6/2013 | |
| KR | 10-2014-0030286 A | 3/2014 | |
| KR | 1020140030286 A | 3/2014 | |
| KR | 10-2014-0103395 A | 8/2014 | |
| KR | 1020140103395 A | 8/2014 | |
| WO | 2006/098885 A1 | 9/2006 | |
| WO | 2014-009715 A1 | 1/2014 | |
| WO | 2014/171779 A1 | 10/2014 | |
| WO | 2014171779 A1 | 10/2014 | |
| WO | WO 2017140780 A1 * | 8/2017 | |

OTHER PUBLICATIONS

F. L. Hirshfeld, "Bonded-Atom Fragments for Describing Molecular Charge Densities", Theoret. Chim. Acta (Berl.) 44, pp. 129-138 (1977).

J. H. Seo et al., "Efficient white organic light-emitting diodes with mixed electron transporting layers", Journal of Mechanical Science and Technology, 25(1), 2011, pp. 17-19.

* cited by examiner

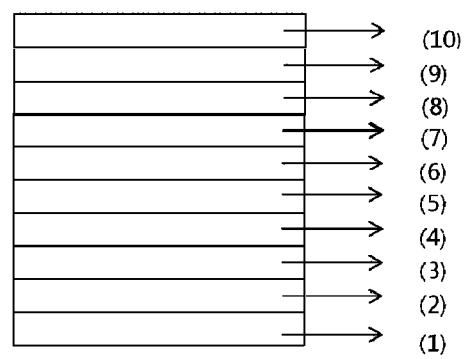

ELECTRON TRANSPORT MATERIALS WITH SELECTED DIPOLE MOMENTS

This application is a National Stage Application of International Application No. PCT/KR2015/011393 filed on Oct. 27, 2015, which claims the benefit of Korean Patent Application No. 10-2014-0146402 filed on Oct. 27, 2014, all of which are hereby incorporated by reference in their entirety for all purposes as if fully set forth herein.

TECHNICAL FIELD

The present specification relates to an organic electroluminescence device.

BACKGROUND ART

An organic electroluminescence device is an electric element which emits light through the current by an applied voltage. Tang et al. reported an organic electroluminescence device having good characteristics in a treatise [Applied Physics Letters 51, p. 913, 1987]. Further, an organic electroluminescence device using a polymeric material while using a structure of the organic electroluminescence device disclosed in the treatise has also been developed.

The key point of the related art as described above is to allow different organic material layers to share roles for performing processes in which an organic electroluminescence device emits light, that is, charge injection, charge transport, formation of optical exciton and generation of light. Therefore, in recent years, there has been used an organic electroluminescence device including a substrate 1, a first electrode 2, a hole injection layer 3, a hole transporting layer 4, a light emitting layer 5, an electron transporting layer 6, an electron injection layer 7, and a second electrode 8, as illustrated in FIG. 1, or an organic electroluminescence device having a structure subdivided into more layers. Meanwhile, various element manufacturing structures are used in electron injection and transporting layers in order to smoothly move electrons from the second electrode to the light emitting layer.

For example, a metal compound belonging to the alkali group, such as LiF, NaF, and LiQ, is frequently used as a material for the electron injection layer, and an organic material basically having a stable structure when electrons move is frequently used in the electron transporting layer. In order to realize a better element efficiency, as a material for the electron transporting layer, materials having a larger band gap than the exciton energy of a light emitting layer and a deep HOMO Level in order to block holes overflowing from the light emitting layer are frequently used.

In order to improve electron injection characteristics of the electron transporting layer, metals and metal compounds belonging to the alkali group, such as Li, Ca, LiF, and LiQ, may also be used with a material for the electron transporting layer to form a layer.

However, these metals and metal compounds belonging to the alkali group each have a small atomic or molecular weight so that there is room for these metals and metal compounds to easily move in the element, which also adversely affects the service life of the element.

DETAILED DESCRIPTION OF THE INVENTION

Technical Problem

The present invention has been made in an effort to provide a technology which does not degrade the service life of an organic electroluminescence device while improving the electron injection characteristics of the element.

Technical Solution

An exemplary embodiment of the present specification provides an organic electroluminescence device including: an anode; a cathode; a light emitting layer provided between the anode and the cathode; and an electron transporting layer provided between the cathode and the light emitting layer, in which the electron transporting layer includes a first electron transporting material and a second electron transporting material, the first electron transporting material is an organic material including a monocyclic or polycyclic ring which includes an N-containing six-membered ring, the second electron transporting material is an organic material including a five-membered hetero ring which includes at least one heteroatom of N, O, and S, or a cyano group, and a dipole moment of the second electron transporting material is larger than a dipole moment of the first electron transporting material.

According to another exemplary embodiment of the present specification, the first electron transporting material has a dipole moment of 0 Debye to 3 Debye, and the second electron transporting material has a dipole moment of 1 Debye to 7 Debye.

According to still another exemplary embodiment of the present specification, the first electron transporting material is an organic material including a monocyclic or polycyclic ring which includes an N-containing six-membered ring.

According to yet another exemplary embodiment of the present specification, the first electron transporting material is an organic material including pyridine, pyrimidine, or triazine.

According to still yet another exemplary embodiment of the present specification, the second electron transporting material is an organic material including a five-membered hetero ring which includes at least one heteroatom of N, O, and S, or a cyano group. The second electron transporting material does not include a six-membered hetero ring.

According to a further exemplary embodiment of the present specification, the second electron transporting material is an organic material including imidazole, oxazole, or thiazole.

According to another further exemplary embodiment of the present specification, the second electron transporting material is an organic material including benzimidazole, benzoxazole, or benzthiazole.

According to still another further exemplary embodiment of the present specification, the first electron transporting material and the second electron transporting material do not include a metal element.

According to yet another further exemplary embodiment of the present specification, the first electron transporting material and the second electron transporting material are an organic material. The first electron transporting material and the second electron transporting material do not include a metal complex.

According to still yet another further exemplary embodiment of the present specification, the first electron transporting material and the second electron transporting material each have a molecular weight of 400 Da to 900 Da.

According to still further exemplary embodiment of the present specification, an electron transporting layer is further included between the electron transporting layer and the cathode.

Advantageous Effects

According to exemplary embodiments described in the present specification, it is possible to provide an organic electroluminescence device having high efficiency and/or long service life characteristics and a simple manufacturing process.

BRIEF DESCRIPTION OF DRAWINGS

FIG. 1 illustrates an example of an organic electroluminescence device composed of a substrate 1, an anode 2, a hole injection layer 5, a hole transporting layer 6, a light emitting layer 7, an electron transporting layer 8, an electron injection layer 9, and a cathode 10.

EXPLANATION OF REFERENCE NUMERALS AND SYMBOLS (1) Substrate
(2) Anode
(5) Hole injection layer
(6) Hole transporting layer
(7) Light emitting layer
(8) Electron transporting layer
(9) Electron injection layer
(10) Cathode

BEST MODE

Hereinafter, the present specification will be described in detail.

The present specification provides an organic electroluminescence device including: an anode; a cathode; a light emitting layer provided between the anode and the cathode; and an electron transporting layer provided between the cathode and the light emitting layer, in which the electron transporting layer includes a first electron transporting material and a second electron transporting material, the first electron transporting material is an organic material including a monocyclic or polycyclic ring which includes an N-containing six-membered ring, the second electron transporting material is an organic material including a five-membered hetero ring which includes at least one heteroatom of N, O, and S, or a cyano group, and a dipole moment of the second electron transporting material is larger than a dipole moment of the first electron transporting material.

When one part "includes" one constituent element in the present specification, unless otherwise specifically described, this does not mean that another constituent element is excluded, but means that another constituent element may be further included.

In the organic electroluminescence device according to an exemplary embodiment of the present specification, it is possible to provide an element having a long service life with improved service life characteristics by a simple manufacturing process by forming an electron transporting layer including two electron transporting materials, which are composed of a first electron transporting material and a second electron transporting material, between a cathode and a light emitting layer.

According to an exemplary embodiment of the present specification, the first electron transporting material and the second electron transporting material are an organic material. Specifically, the first electron transporting material is an organic material including a monocyclic or polycyclic ring which includes an N-containing six-membered ring, and the second electron transporting material is an organic material including a five-membered hetero ring which includes at least one heteroatom of N, O, and S, or a cyano group.

In an exemplary embodiment of the present specification, the first electron transporting material and the second electron transporting material do not substantially include a metal element or a metal complex. Accordingly, it is possible to prevent a problem in that a metal element or a metal complex degrades the service life of an element.

In the organic electroluminescence device according to an exemplary embodiment of the present specification, a dipole moment of the second electron transporting material is larger than a dipole moment of the first electron transporting material.

In the present specification, the dipole moment is a physical quantity which indicates the degree of polarity, and may be calculated by the following Equation 1.

$$p(r) = \int_V \rho(r_0)(r_0 - r)d^3r_0 \qquad \text{[Equation 1]}$$

$\rho(r_0)$: molecular density
V: volume
r: the point of observation
$d^3r_0$: an elementary volume The value of the dipole moment may be obtained by calculating the molecular density in Equation 1. For example, the molecular density may be obtained by using a method called Hirshfeld Charge Analysis to obtain a charge and a dipole for each atom and performing the calculation according to the following equations, and the dipole moment may be obtained by substituting the Equation 1 with the calculation result.

Weight Function $$W_\alpha(r) = \rho_\alpha(r - R_\alpha) \left[ \sum_\beta \rho_\beta(r - R_\beta) \right]^{-1}$$

$\rho_\alpha(r - R_\alpha)$: spherically averaged ground-state atomic density $\sum_\beta \rho_\beta(r - R_\beta)$ : promolecule density Deformation Density $$\rho_d(r) = \rho(r) - \sum_\alpha \rho_\alpha(r - R_\alpha)$$

ρ(r): molecular density
$\rho_\alpha$ (r-$R_\alpha$): density of the free atom a located at coordinates $R_\alpha$ Atomic Charge $q(\alpha) = \int \rho_d(r) W_\alpha(r) d^3r$ $W_\alpha(r)$: weight function The dipole moment may be calculated with reference to [F. L. Hirshfeld (1977). "Bonded Atom Fragments for Describing Molecular Charge Densities". Theoret. Chim. Acta (Berl.) 44: 129-138.] which is a treatise by Hirshfeld Charge Analysis.

In an exemplary embodiment of the present specification, the first electron transporting material has a dipole moment of 0 Debye to 3 Debye, and the second electron transporting material has a dipole moment of 1 Debye to 7 Debye. The first electron transporting material having a dipole moment of 0 Debye to 3 Debye may increase the driving voltage while positively affecting the service life. In contrast, the second electron transporting material having a larger dipole moment than the first electron transporting material may provide an element having excellent efficiency at a low driving voltage.

The organic electroluminescence device according to an exemplary embodiment of the present specification may include both the first electron transporting material having a dipole moment of 0 Debye to 3 Debye and the second electron transporting material having a dipole moment of 1 Debye to 7 Debye, thereby providing an element having a low driving voltage, service life characteristics of the element, and high efficiency.

In an exemplary embodiment of the present specification, examples of the compound having a dipole moment of 0 Debye to 3 Debye include an organic material including a monocyclic or polycyclic ring which includes an N-containing six-membered ring. Examples of the compound having a dipole moment of 1 Debye to 7 Debye include an organic material including a five-membered hetero ring which includes N, O, or S, or a cyano group. The present exemplary embodiment is characterized in that two or more organic materials having different dipole moment values are included in one organic material layer, as described above.

In the present specification, the meaning of the "organic material including a monocyclic or polycyclic ring which includes an N-containing six-membered ring" or "organic material including a five-membered hetero ring which includes at least one heteroatom of N, O, and S, or a cyano group" may mean not only the case where the organic material is included as a core structure in the structure of the organic material, but also the case where the organic material is included as a substituent.

According to another exemplary embodiment, the first electron transporting material is an organic material including a monocyclic or polycyclic ring which includes an N-containing six-membered ring. The N-containing six-membered ring may be represented by the following Formula.

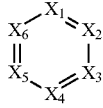

[Formula 1]

In the Formula,
one to three of $X_1$ to $X_6$ is (are) N,
the others are $CR_1$ and $R_1$ is a monovalent organic group, and
adjacent monovalent organic groups may combine with each other to form a substituted or unsubstituted aliphatic ring or a substituted or unsubstituted aromatic ring.

According to still another exemplary embodiment, the first electron transporting material is an organic material including pyridine, pyrimidine, or triazine.

In an exemplary embodiment of the present specification, $X_2$ is $CR_1$.

In another exemplary embodiment, $X_4$ is $CR_1$.

In still another exemplary embodiment, $X_6$ is $CR_1$.

According to yet another exemplary embodiment, the first electron transporting material may be represented by the following Formula 2.

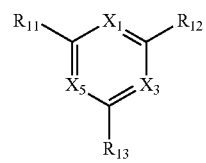

[Formula 2]

In Formula 2,
at least one of $X_1$, $X_3$, and $X_5$ is N and the others are $CR_1$,
$R_1$ and $R_{11}$ to $R_{13}$ are the same as or different from each other, and are each a monovalent organic group, and
adjacent monovalent organic groups may combine with each other to form a substituted or unsubstituted aliphatic ring or a substituted or unsubstituted aromatic ring.

According to still yet another exemplary embodiment, Formula 2 may be represented by the following Formula 3.

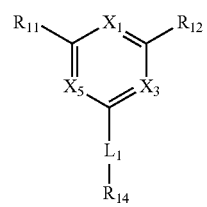

[Formula 3]

In Formula 3,
at least one of $X_1$, $X_3$, and $X_5$ is N and the others are $CR_1$,
$R_1$, $R_{11}$, $R_{12}$, and $R_{14}$ are the same as or different from each other, and are each a monovalent organic group,
$L_1$ is a divalent organic group, and
adjacent monovalent organic groups or adjacent divalent organic groups may combine with each other to form a substituted or unsubstituted aliphatic ring or a substituted or unsubstituted aromatic ring.

According to a further exemplary embodiment, Formula 2 may be represented by the following Formula 4.

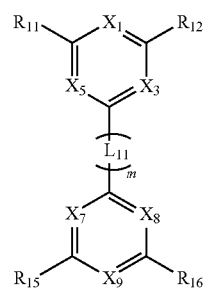

[Formula 4]

In Formula 4,
at least one of $X_1$, $X_3$, $X_5$, and $R_7$ to $R_9$ is N and the others are $CR_1$,
$R_1$, $R_{11}$, $R_{12}$, and $R_{14}$ to $R_{16}$ are the same as or different from each other, and are each a monovalent organic group,
$L_{11}$'s are the same as or different from each other, and are each a divalent organic group, and m is an integer of 1 to 3, and adjacent monovalent organic groups or adjacent divalent organic groups may combine with each other to form a substituted or unsubstituted aliphatic ring or a substituted or unsubstituted aromatic ring.

According to another further exemplary embodiment, the second electron transporting material is an organic material including a five-membered hetero ring which includes at least one heteroatom of N, O, and S, or a cyano group. The second electron transporting material does not include a six-membered hetero ring.

According to still another further exemplary embodiment, the five-membered hetero ring may be represented by the following Formula 5.

[Formula 5]

In Formula 5, $Y_1$ is $NR_{21}$, O, or S, $Y_2$ to $Y_5$ are the same as or different from each other, and are each N or $CR_{22}$, $R_{21}$ and $R_{22}$ are the same as or different from each other, and are each a monovalent organic group, and adjacent monovalent organic groups may combine with each other to form a substituted or unsubstituted aliphatic ring or a substituted or unsubstituted aromatic ring.

According to yet another further exemplary embodiment, the second electron transporting material is an organic material including imidazole, oxazole, or thiazole.

In an exemplary embodiment of the present specification, $Y_5$ is $CR_{22}$.

In another exemplary embodiment, $Y_4$ is $CR_{22}$.

In an exemplary embodiment of the present specification, $Y_5$ and $Y_4$ are each $CR_{22}$, and $R_{22}$'s may combine with each other to form a substituted or unsubstituted aliphatic ring or a substituted or unsubstituted aromatic ring.

In an exemplary embodiment of the present specification, $Y_5$ and $Y_4$ are each $CR_{22}$, and $R_{22}$'s may combine with each other to form a substituted or unsubstituted aromatic ring.

In an exemplary embodiment of the present specification, $Y_5$ and $Y_4$ are each $CR_{22}$, and $R_{22}$'s may combine with each other to form a substituted or unsubstituted benzene ring.

According to another exemplary embodiment, the second electron transporting material may be represented by the following Formula 6.

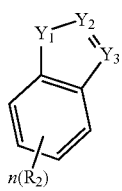

[Formula 6]

In Formula 6, $Y_1$ is $NR_{21}$, O, or S, $Y_2$ and $Y_3$ are the same as or different from each other, and are each N or $CR_{22}$, $R_2$, $R_{21}$, and $R_{22}$ are the same as or different from each other, and are each a monovalent organic group, n is an integer of 0 to 4, and adjacent monovalent organic groups may combine with each other to form a substituted or unsubstituted aliphatic ring or a substituted or unsubstituted aromatic ring.

In an exemplary embodiment of the present specification, $Y_2$ is $CR_{22}$.

According to another exemplary embodiment, Formula 6 may be represented by the following Formula 7.

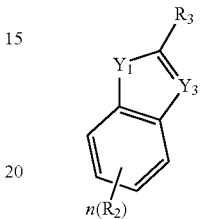

[Formula 7]

In Formula 7, $Y_1$ is $NR_{21}$, O, or S, $Y_3$ is N or $CR_{22}$, $R_2$, $R_3$, $R_{21}$, and $R_{22}$ are the same as or different from each other, and are each a monovalent organic group, n is an integer of 0 to 4, and adjacent monovalent organic groups may combine with each other to form a substituted or unsubstituted aliphatic ring or a substituted or unsubstituted aromatic ring.

According to another exemplary embodiment of the present specification, the second electron transporting material is an organic material including benzimidazole, benzoxazole, or benzthiazole.

In another exemplary embodiment, $Y_1$ is O.

In still another exemplary embodiment, $Y_1$ is S.

In yet another exemplary embodiment, $Y_1$ is $NR_{21}$.

In an exemplary embodiment of the present specification, $Y_3$ is N.

According to another exemplary embodiment of the present specification, Formula 7 may be represented by any one of the following Formulae 8 to 10.

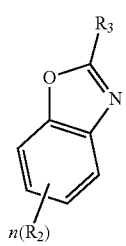

[Formula 8]

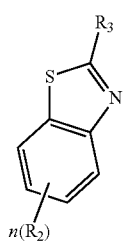

[Formula 9]

-continued

[Formula 10]

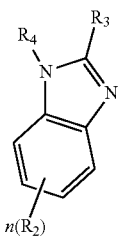

In Formulae 8 to 10, $R_2$, $R_3$, and $R_4$ are the same as or different from each other, and are each a monovalent organic group, n is an integer of 0 to 4, and adjacent monovalent organic groups may combine with each other to form a substituted or unsubstituted aliphatic ring or a substituted or unsubstituted aromatic ring.

According to another exemplary embodiment, Formula 7 may be represented by the following Formula 11.

[Formula 11]

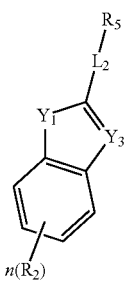

In Formula 11, $Y_1$ is $NR_{21}$, O, or S, $Y_3$ is N or $CR_{22}$, $R_2$, $R_5$, $R_{21}$, and $R_{22}$ are the same as or different from each other, and are each a monovalent organic group, n is an integer of 0 to 4, and adjacent monovalent organic groups may combine with each other to form a substituted or unsubstituted aliphatic ring or a substituted or unsubstituted aromatic ring.

According to another exemplary embodiment, Formula 7 may be represented by the following Formula 12.

[Formula 12]

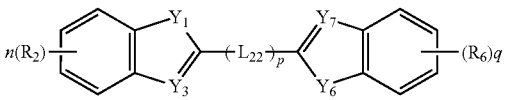

In Formula 12, $Y_1$ and $Y_6$ are the same as or different from each other, and are each $NR_{21}$, O, or S, $Y_3$ and $Y_7$ are the same as or different from each other, and are each N or $CR_{22}$, $R_2$, $R_6$, $R_{21}$, and $R_{22}$ are the same as or different from each other, and are each a monovalent organic group, n and q are each an integer of 0 to 4, $L_{22}$'s are the same as or different from each other, and are each a divalent organic group, and p is an integer of 1 to 3, and adjacent monovalent organic groups or adjacent divalent organic groups may combine with each other to form a substituted or unsubstituted aliphatic ring or a substituted or unsubstituted aromatic ring.

According to still another exemplary embodiment, Formula 7 may be represented by the following Formula 13.

[Formula 13]

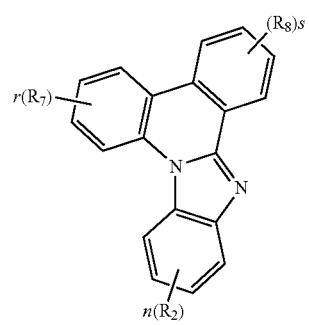

In Formula 13, $R_2$, $R_7$, and $R_8$ are the same as or different from each other, and are each a monovalent organic group, n, r, and s are each an integer of 0 to 4, and adjacent monovalent organic groups may combine with each other to form a substituted or unsubstituted aliphatic ring or a substituted or unsubstituted aromatic ring.

According to yet another exemplary embodiment, a compound including a cyano group as the second electron transporting material may be represented by the following Formula 14.

$$CN\text{-}(L_{31})_t\text{-}R_{31}$$ [Formula 14]

In Formula 14, $L_{31}$ is a divalent organic group and t is an integer of 0 to 4, and when t is 2 or more, $L_{31}$'s are the same as or different from each other, and $R_{31}$ is a monovalent organic group.

In an exemplary embodiment of the present specification, $L_{31}$ includes a substituted or unsubstituted anthracene.

According to another exemplary embodiment, Formula 14 may be represented by the following Formula 15.

[Formula 15]

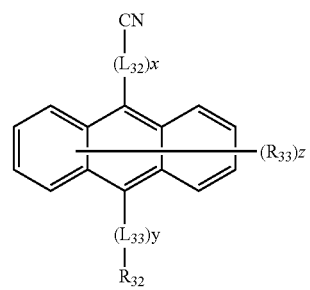

In Formula 15, $L_{32}$ and $L_{33}$ are a divalent organic group, and $R_{32}$ and $R_{33}$ are a monovalent organic group, and x and y are an integer of 0 to 4 and z is an integer of 0 to 8, and when x, y, or z is 2 or more, the structures in the parenthesis are the same as or different from each other.

In an exemplary embodiment of the present specification, $L_{32}$ is a phenylene group.

In another exemplary embodiment, $L_{33}$ is a phenylene group.

According to still another exemplary embodiment, Formula 15 may be represented by the following Formula 16.

[Formula 16]

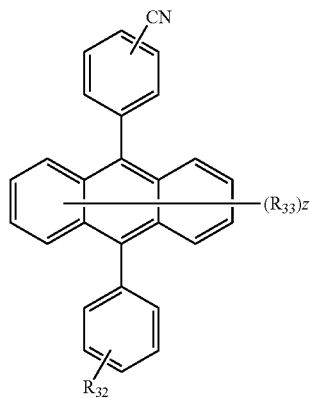

In Formula 16, z, $R_{32}$, and $R_{33}$ are the same as those defined in Formula 15.

In the present specification, examples of the organic group include an alkyl group, an alkenyl group, a cycloalkyl group, a cycloalkenyl group, an aryl group, an aralkyl group, and the like. The organic group may include a bond or a substituent other than a hydrocarbon group such as a heteroatom in the organic group. Further, the organic group may be any one of a straight-chained organic group, a branched organic group, and a cyclic organic group.

In the present specification, the monovalent organic group means a monovalent group having one bonding position in an organic compound.

In the present specification, the divalent organic group means a divalent group having two bonding positions in an organic compound.

The organic group may also form a cyclic structure, and may form a bond by including a heteroatom as long as the effects of the invention are not impaired. Specifically, examples thereof include a bond including a heteroatom such as an oxygen atom, a nitrogen atom, and a silicon atom. Specific examples thereof include a cyano bond, an ether bond, a thioether bond, a carbonyl bond, a thiocarbonyl bond, an ester bond, an amide bond, a urethane bond, an imino bond (—N═C(-A)-, —C(═NA)-: A represents a hydrogen atom or an organic group), a carbonate bond, a sulfonyl bond, a sulfinyl bond, an azo bond, and the like, and are not limited thereto.

The cyclic structure may be the aromatic ring, the aliphatic ring, and the like as described above, and may be monocyclic or polycyclic.

According to an exemplary embodiment of the present specification, in Formulae 1 to 16, the monovalent organic group is hydrogen; deuterium; a halogen group; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted arylphosphine group; a substituted or unsubstituted phosphine oxide group; a substituted or unsubstituted aryl group; or a substituted or unsubstituted aromatic or aliphatic heterocyclic group.

According to an exemplary embodiment, in Formulae 1 to 16, the monovalent organic group is a substituted or unsubstituted aryl group; or a substituted or unsubstituted aromatic or aliphatic heterocyclic group.

According to an exemplary embodiment, when the monovalent organic group is substituted, the monovalent organic group may be substituted with one or more substituents selected from the group consisting of a substituted or unsubstituted aryl group; and a substituted or unsubstituted aromatic or aliphatic heterocyclic group.

According to an exemplary embodiment, when the monovalent organic group is substituted, the monovalent organic group may be substituted with one or more substituents selected from the group consisting of an aryl group; a dialkylfluorenyl group; a spirobifluorenyl group; a carbazole group; a benzocarbazole group; and an aromatic or aliphatic heterocyclic group.

In an exemplary embodiment of the present specification, the monovalent organic group may be a phenyl group, a naphthyl group, a biphenyl group, a terphenyl group, a dialkylfluorenyl group, a phenanthrenyl group, a spirobifluorenyl group, an anthracenyl group, or an alkyl group having 1 to 10 carbon atoms, and the phenyl group, the naphthyl group, the biphenyl group, the terphenyl group, the dialkylfluorenyl group, the phenanthrenyl group, the spirobifluorenyl group, the anthracenyl group, and the alkyl group having 1 to 10 carbon atoms are substituted with one or two more substituents selected from the group consisting of a phenyl group, a naphthyl group, a biphenyl group, a terphenyl group, a dialkylfluorenyl group, a phenanthrenyl group, a spirobifluorenyl group, an anthracenyl group, a pyridine group, a triazine group, a quinoline group, a carbazole group, a benzocarbazole group, a benzimidazole group, a benzoxazole group, a benzothiazole group, a spirofluorene indolo acridine group, and an alkyl group having 1 to 10 carbon atoms, or are substituted with a substituent to which two or more substituents are linked.

According to an exemplary embodiment, in Formulae 1 to 16, the divalent organic group is a substituted or unsubstituted arylene group; or a substituted or unsubstituted aromatic or aliphatic divalent heterocyclic group.

According to an exemplary embodiment, when the divalent organic group is substituted, the divalent organic group may be substituted with one or more substituents selected from the group consisting of a substituted or unsubstituted aryl group; and a substituted or unsubstituted aromatic or aliphatic heterocyclic group.

According to an exemplary embodiment, when the divalent organic group is substituted, the divalent organic group may be substituted with one or more substituents selected from the group consisting of an aryl group; a dialkylfluorenyl group; a spirobifluorenyl group; a carbazole group; a benzocarbazole group; and an aromatic or aliphatic heterocyclic group.

According to an exemplary embodiment of the present specification, the divalent organic group is a phenylene group, a naphthylene group, a biphenylylene group, a terphenylene group, a dialkylfluorenylene group, a phenanthrenylene group, a spirobifluorenylene group, or an anthracenylene group, and the phenylene group, the naphthylene group, the biphenylylene group, the terphenylene group, the dialkylfluorenylene group, the phenanthrenylene group, the spirobifluorenylene group, and the anthracenylene group are substituted with one or two or more substituents selected from the group consisting of a phenyl group, a naphthyl group, a biphenyl group, a terphenyl group, a dialkylfluorenyl group, a phenanthrenyl group, a spirobifluorenyl group, an anthracenyl group, a pyridine group, a triazine group, a quinoline group, a carbazole group, a benzocarbazole group, a benzimidazole group, a benzoxazole group, a benzothiazole group, a spirofluorene indolo acridine group, and an alkyl group having 1 to 10 carbon atoms, or are substituted with a substituent to which two or more substituents are linked.

Examples of the substituents will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means that a group is substituted with one or two or more substituents selected from the group consisting of deuterium; a halogen group; a nitrile group; a nitro group; an imide group; an amide group; a hydroxy group; a substituted or unsubstituted alkyl group; a substituted or unsubstituted cycloalkyl group; a substituted or unsubstituted alkoxy group; a substituted or unsubstituted alkenyl group; a substituted or unsubstituted amine group; a substituted or unsubstituted aryl group; and a substituted or unsubstituted heterocyclic group or is substituted with a substituent to which two or more substituents are linked among the substituents exemplified above, or has no substituent. For example, "the substituent to which two or more substituents are linked" may be a biphenyl group. That is, the biphenyl group may also be an aryl group, and may be interpreted as a substituent to which two phenyl groups are linked.

In the present specification, examples of a halogen group include fluorine, chlorine, bromine or iodine.

In the present specification, in an ester group, the oxygen of the ester group may be substituted with a straight-chained, branched, or cyclic alkyl group having 1 to 25 carbon atoms, or an aryl group having 6 to 25 carbon atoms. Specifically, the ester group may be a compound having the following structural formulae, but is not limited thereto.

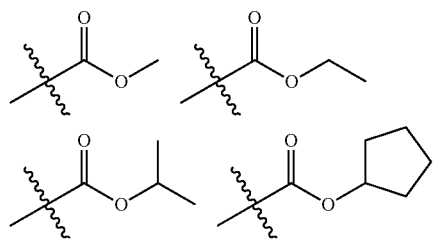

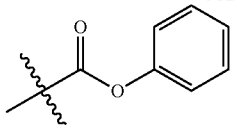

In the present specification, the number of carbon atoms of an imide group is not particularly limited, but is preferably 1 to 25. Specifically, the imide group may be a compound having the following structures, but is not limited thereto.

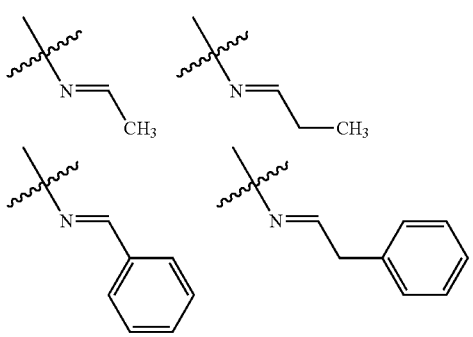

In the present specification, in the amide group, nitrogen of the amide group may be substituted with hydrogen, a straight-chained, branched, or cyclic alkyl group having 1 to 25 carbon atoms, or an aryl group having 6 to 25 carbon atoms. Specifically, the amide group may be a compound having the following structural formulae, but is not limited thereto.

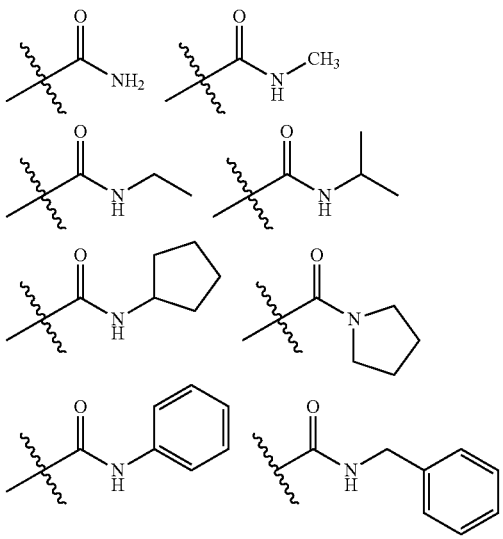

In the present specification, the alkyl group may be straight-chained or branched, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the cycloalkyl group is not particularly limited, but the number of carbon atoms thereof is preferably 3 to 60, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight-chained, branched, or cyclic. The number of carbon atoms of the alkoxy group is not particularly limited, but is preferably 1 to 20. Specific examples thereof include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the alkenyl group may be straight-chained or branched, and the number of carbon atoms thereof is not particularly limited, but is preferably 2 to 40. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

When the aryl group is a monocyclic aryl group, the number of carbon atoms thereof is not particularly limited, but is preferably 6 to 25. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 24. Specific examples of the polycyclic aryl group include a naphthyl group, an anthryl group, a phenanthryl group, a pyrenyl group, a perylenyl group, a chrysenyl group, a fluorenyl group, and the like, but are not limited thereto.

In the present specification, the fluorenyl group may be substituted, and adjacent substituents may combine with each other to form a ring.

When the fluorenyl group is substituted, the fluorenyl group may be

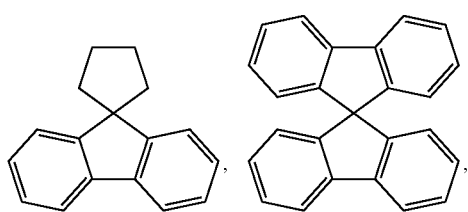

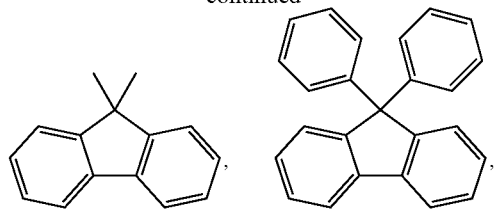

and the like. However, the group is not limited thereto.

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, the number of carbon atoms of the amine group is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group, and the like, but are not limited thereto.

In the present specification, examples of the arylamine group include a substituted or unsubstituted monoarylamine group, a substituted or unsubstituted diarylamine group, and a substituted or unsubstituted triarylamine group. The aryl group in the arylamine group may be a monocyclic aryl group, and may be a polycyclic aryl group. The arylamine group having the two or more aryl groups may include a monocyclic aryl group, a polycyclic aryl group, or both a monocyclic aryl group and a polycyclic aryl group.

Specific examples of the arylamine group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group, and the like, but are not limited thereto.

In the present specification, examples of the arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group, and may be a polycyclic aryl group. The arylphosphine group including the two or more aryl groups may include a monocyclic aryl group, a polycyclic aryl group, or both a monocyclic aryl group and a polycyclic aryl group.

In the present specification, the heterocyclic group includes one or more of an atom other than carbon, that is, a heteroatom, and specifically, the heteroatom may include one or more atoms selected from the group consisting of O, N, Se, and S, and the like. The number of carbon atoms thereof is not particularly limited, but is preferably 2 to 60. Examples of the heterocyclic group include a thiophene group, a furan group, a pyrrole group, an imidazole group, a triazole group, an oxazole group, an oxadiazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazole group, a benzocarbazole group, a benzothiophene group, a dibenzothiophene group, a benzofuranyl group, a phenanthroline group, a thiazolyl group, an isooxazolyl group, an oxadiazolyl group, a thiadiazolyl group, a benzothiazolyl group, a phenothiazinyl group, a dibenzofuranyl group, and the like, but are not limited thereto.

In the present specification, the aryl group in the aryloxy group, the arylthioxy group, the arylsulfoxy group, and the aralkylamine group is the same as the above-described example of the aryl group. Specifically, examples of the aryloxy group include phenoxy, p-tolyloxy, m-tolyloxy, 3,5-dimethyl-phenoxy, 2,4,6-trimethylphenoxy, p-tert-butylphenoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, 9-phenanthryloxy, and the like, examples of the arylthioxy group include a phenylthioxy group, a 2-methylphenylthioxy group, a 4-tert-butylphenylthioxy group, and the like, and examples of the arylsulfoxy group include a benzenesulfoxy group, a p-toluenesulfoxy group, and the like, but the examples are not limited thereto.

In the present specification, the alkyl group in the alkylthioxy group and the alkylsulfoxy group is the same as the above-described examples of the alkyl group. Specifically, examples of the alkylthioxy group include a methylthioxy group, an ethylthioxy group, a tert-butylthioxy group, a hexylthioxy group, an octylthioxy group, and the like, and examples of the alkylsulfoxy group include mesyl, an ethylsulfoxy group, a propylsulfoxy group, a butylsulfoxy group, and the like, but are not limited thereto.

According to an exemplary embodiment of the present specification, as the first electron transporting material, one or two or more of the organic materials represented by the following Formulae cp6-1 to cp6-24 may be selected.

[cp6-1]

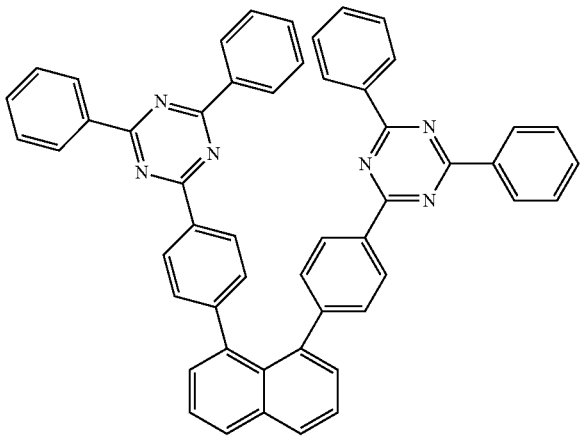

[cp6-2]

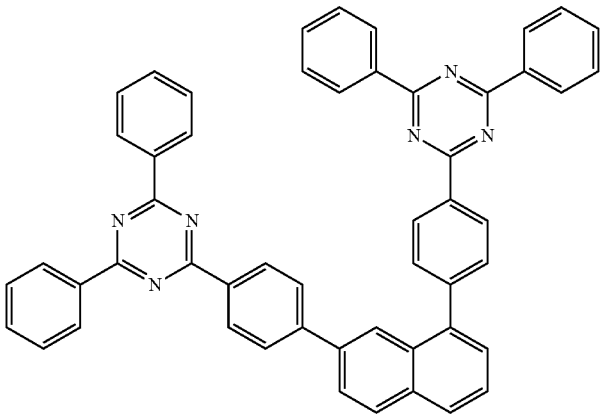

[cp6-3]
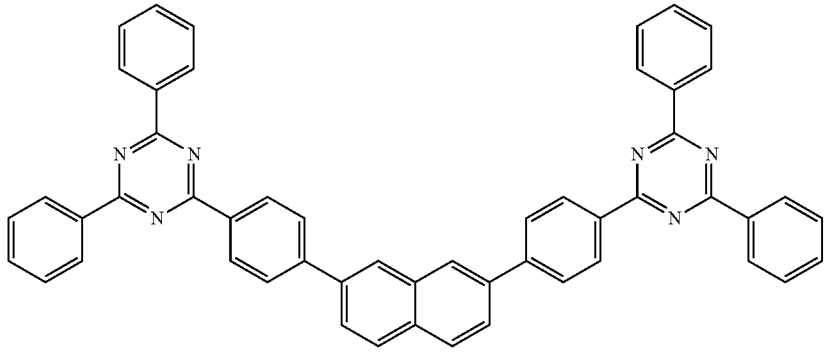
[cp6-4]
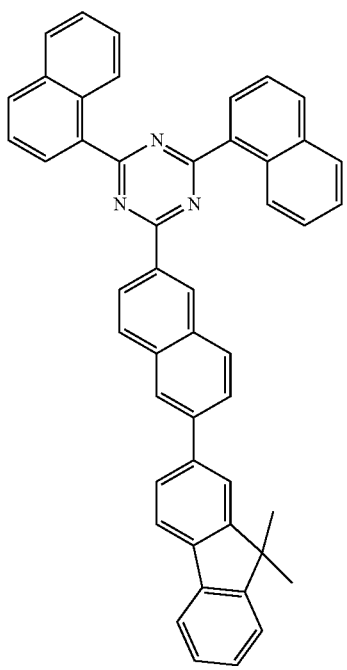
[cp6-5]
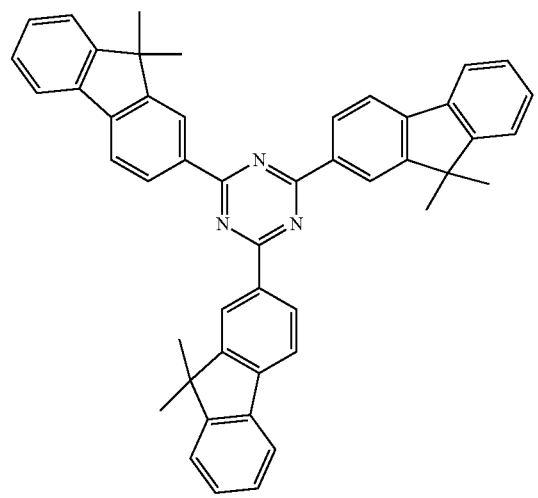
[cp6-6]
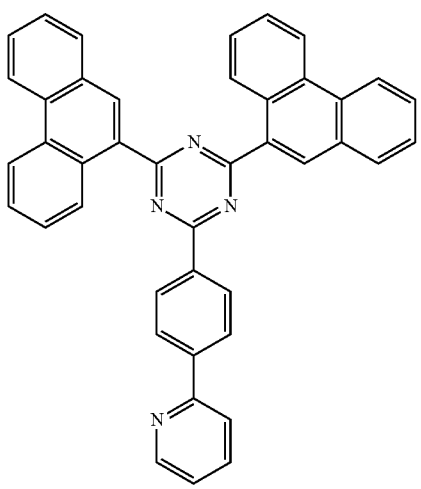
[cp6-7]
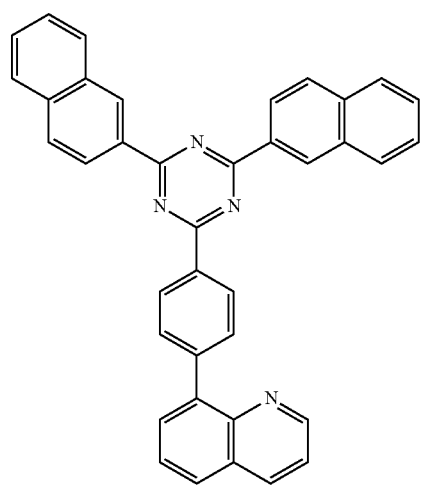

-continued
[cp6-8]
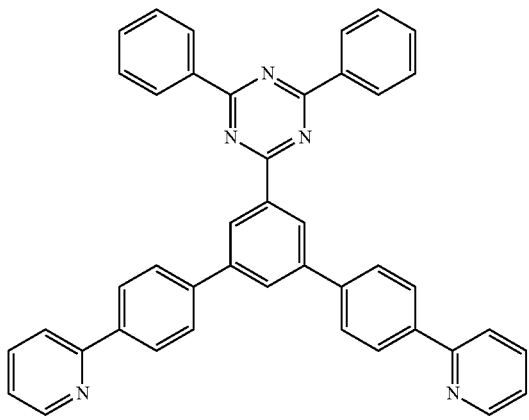
[cp6-9]
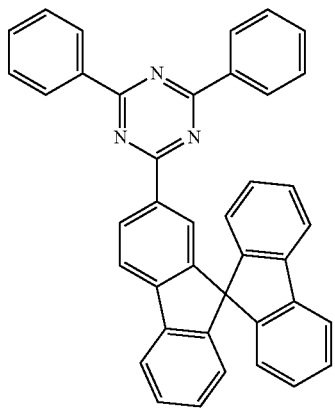
[cp6-10]
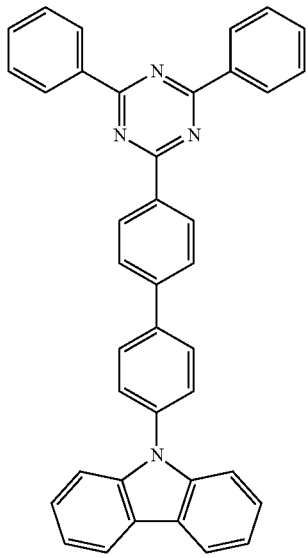
[cp6-11]
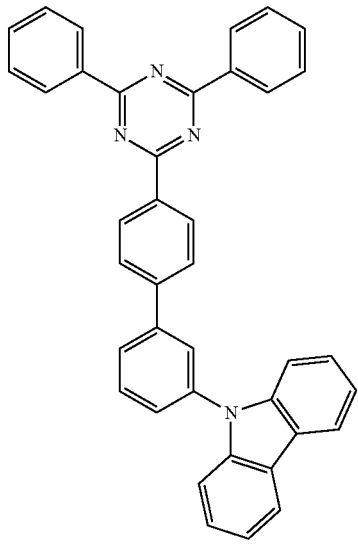
[cp6-12]
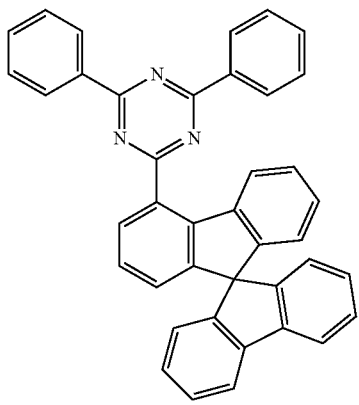
[cp6-13]
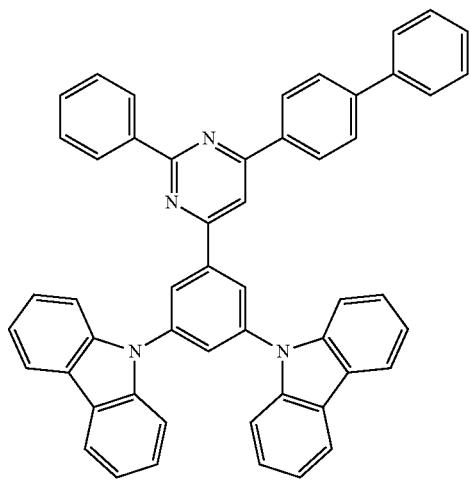

-continued
[cp6-14]
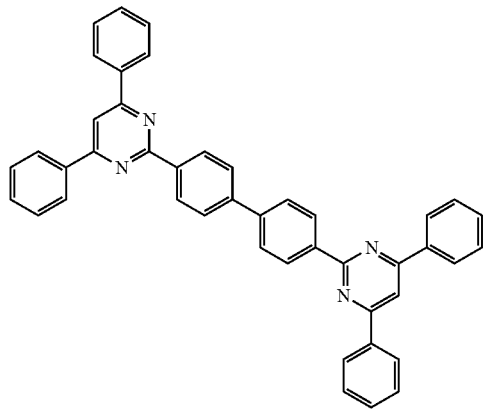
[cp6-15]
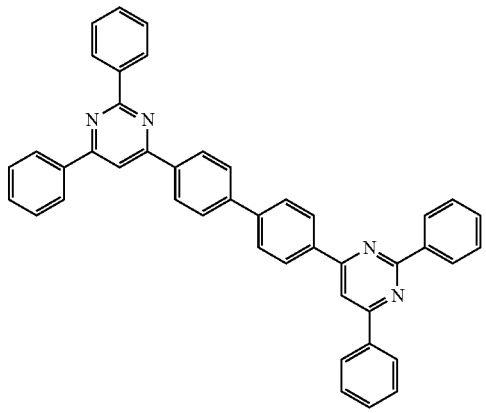
[cp6-16]
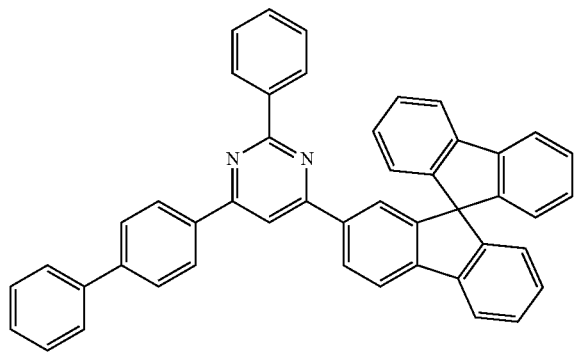
[cp6-17]
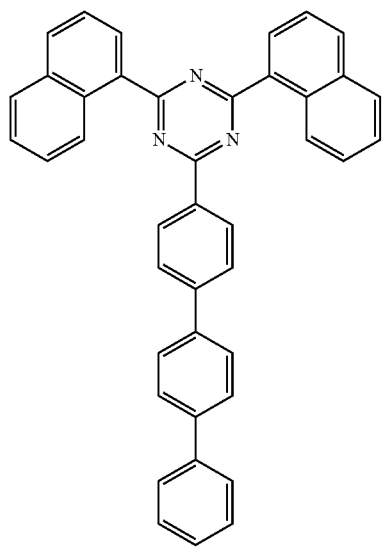

-continued
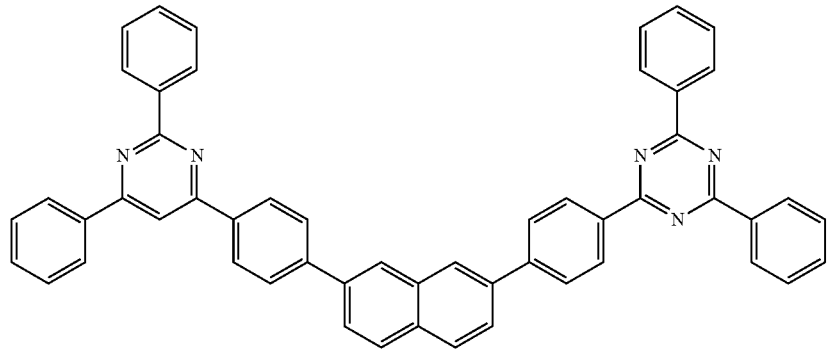
[cp6-18]
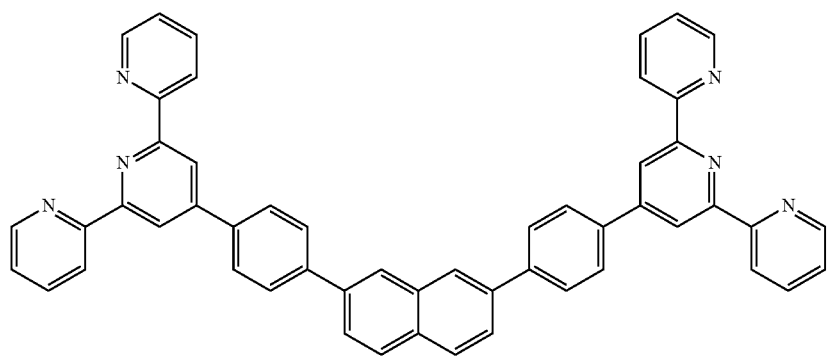
[cp6-19]
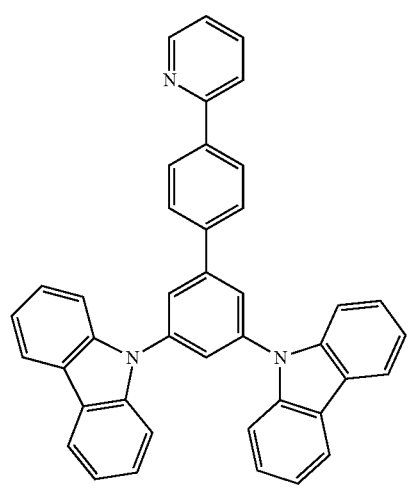
[cp6-20]

-continued
[cp6-21]
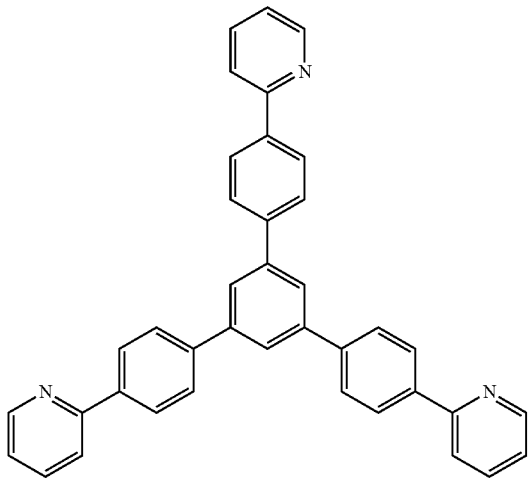
[cp6-22]
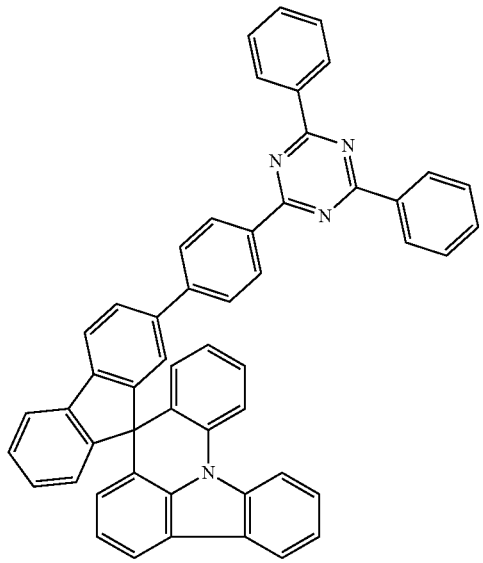
[cp6-23]
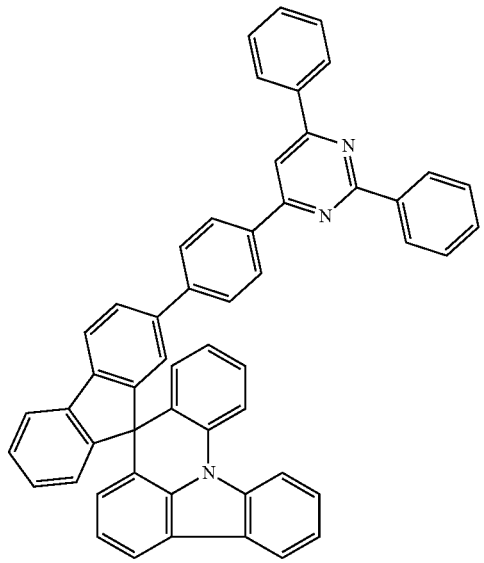
[cp6-24]
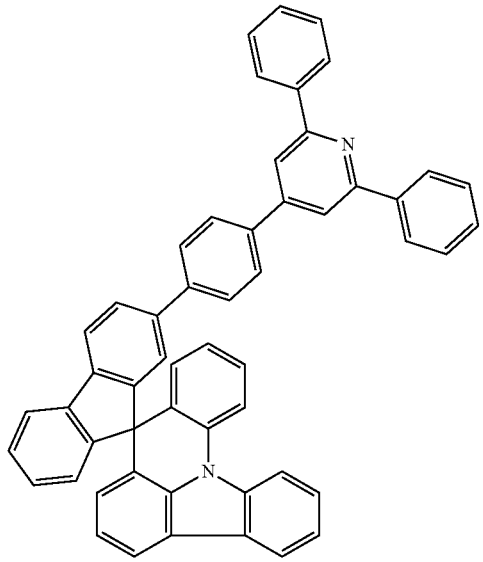

According to an exemplary embodiment of the present specification, as the second electron transporting material, one or two or more of the organic materials represented by the following Formulae cp7-1 to cp7-21 may be selected.
[cp7-1]
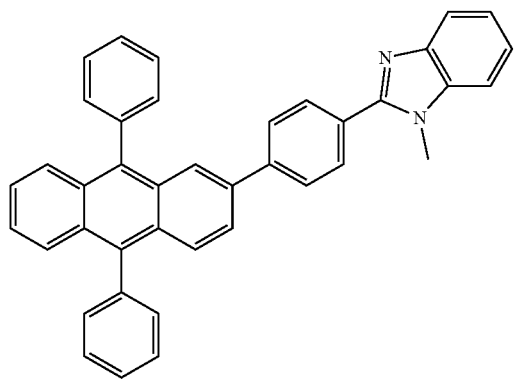
[cp7-2]
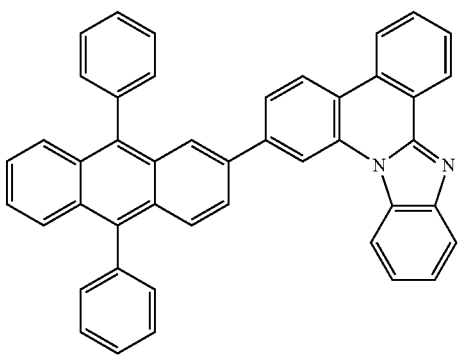
[cp7-3]
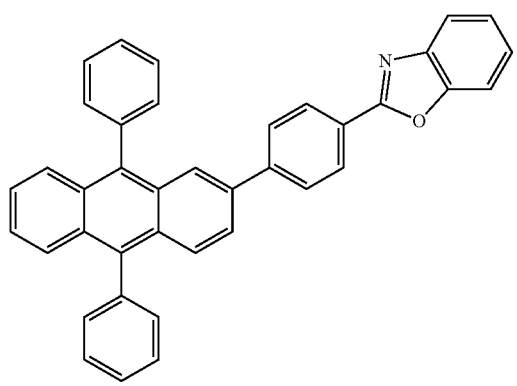
[cp7-4]
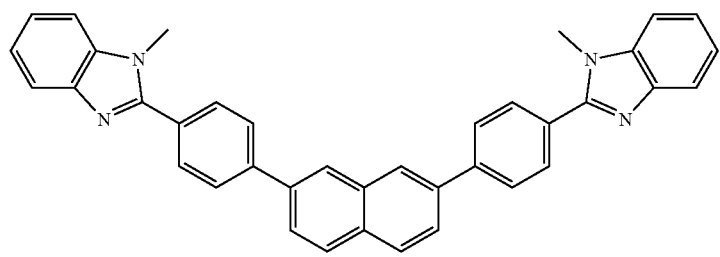

-continued
[cp7-5]
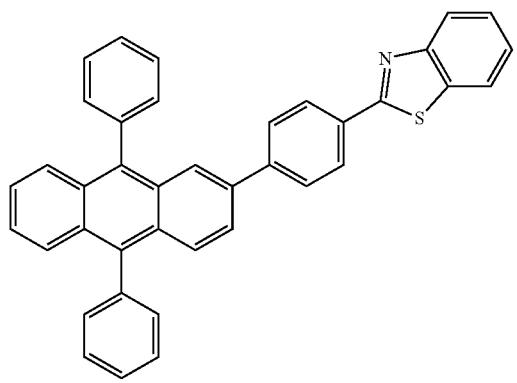
[cp7-6]
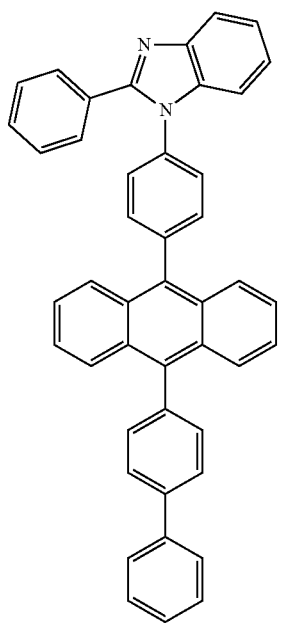
[cp7-7]
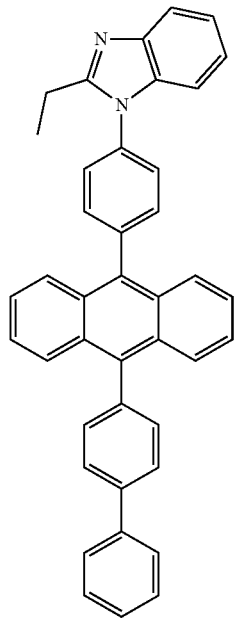
[cp7-8]
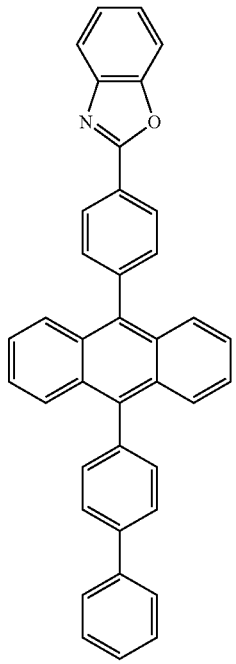

[cp7-9]
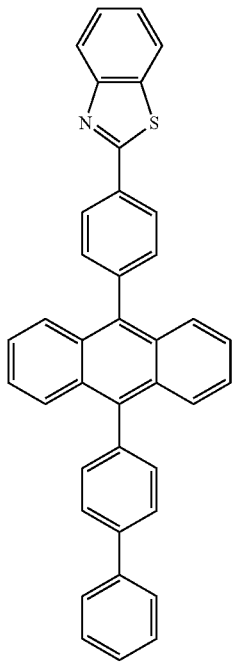
[cp7-10]
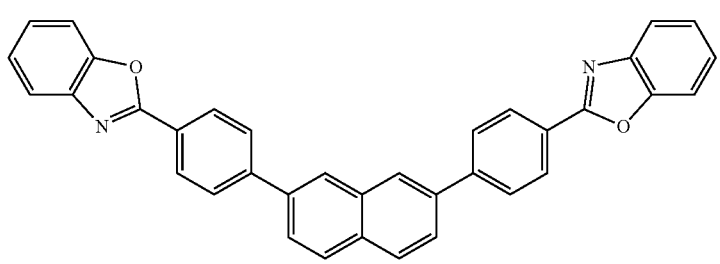
[cp7-11]
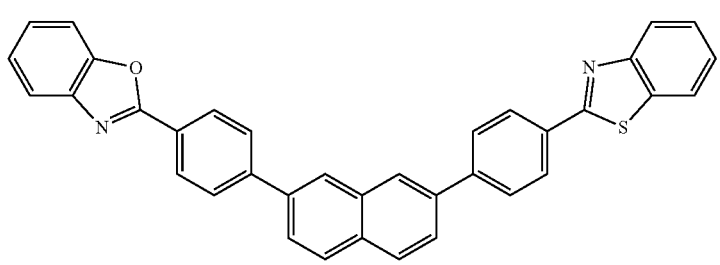
[cp7-12]
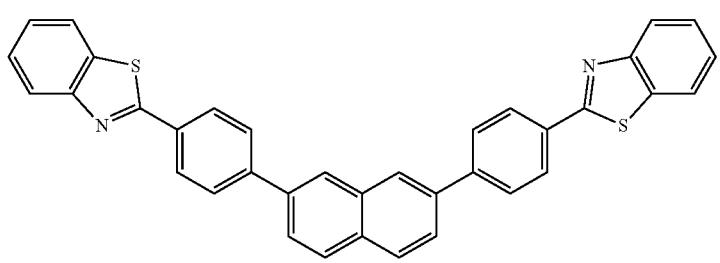

-continued
[cp7-13]
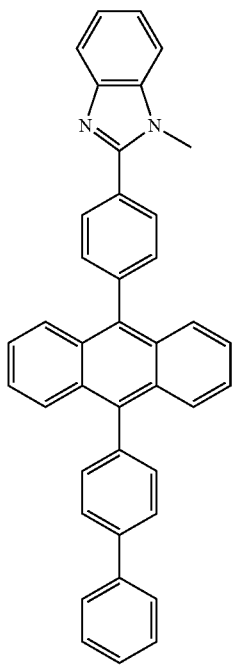
[cp7-14]
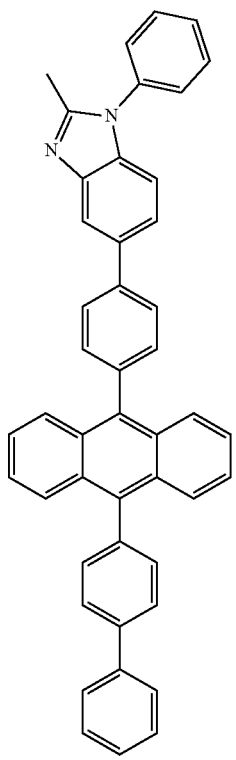
[cp7-15]
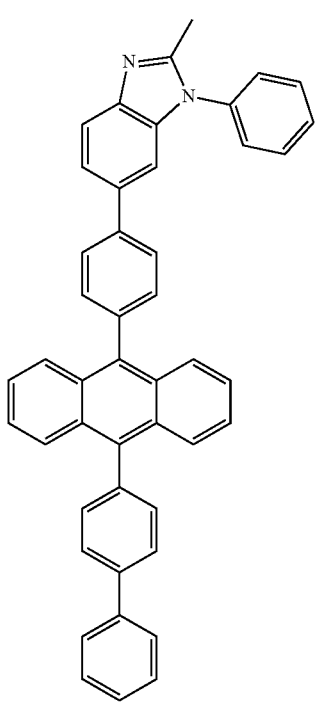

-continued
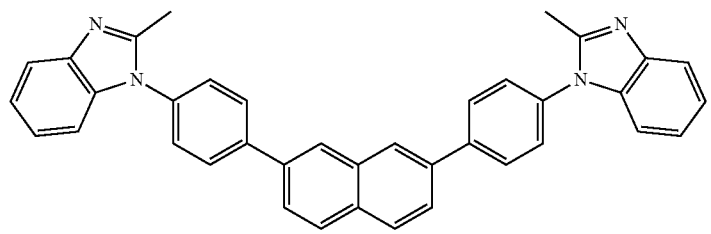
[cp7-16]
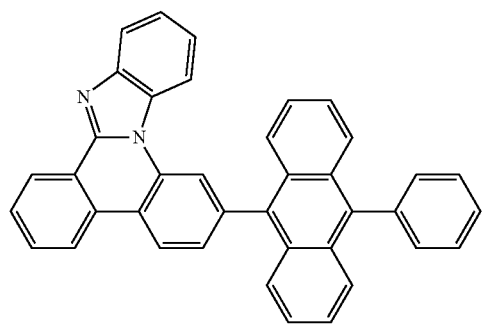
[cp7-17]
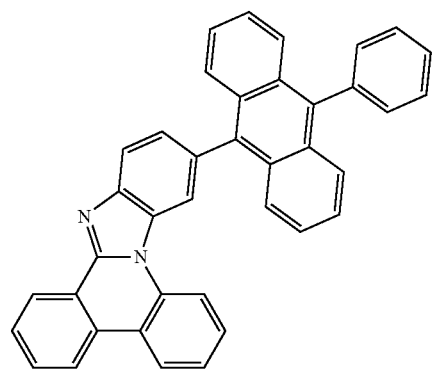
[cp7-18]
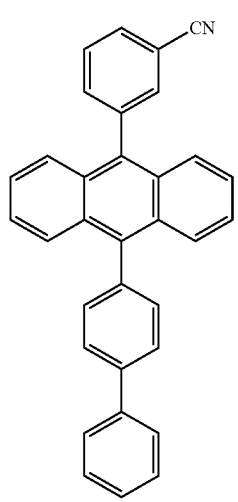
[cp7-19]
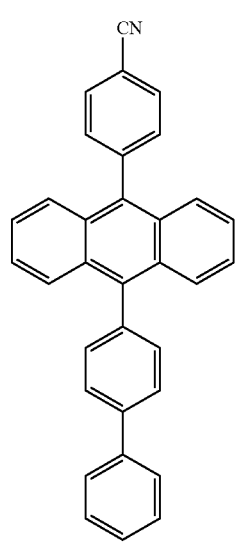
[cp7-20]

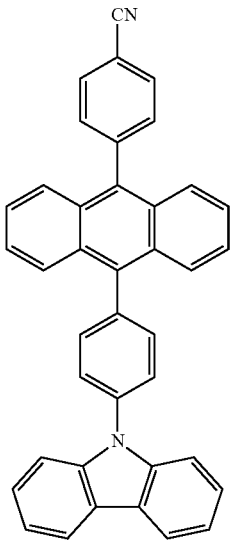

[cp7-21]

The dipole moment values of some of the compounds are as follows.

TABLE 1

| Compound | Dipole moment |
|---|---|
| cp6-1 | 0.44 |
| cp6-2 | 0.45 |
| cp6-3 | 0.32 |
| cp6-4 | 1.43 |
| Cp6-5 | 0.20 |
| cp6-8 | 1.71 |
| cp6-10 | 1.76 |
| cp6-13 | 2.54 |
| cp6-22 | 1.01 |
| cp7-1 | 3.75 |
| cp7-2 | 3.67 |
| cp7-3 | 1.56 |
| cp7-4 | 4.46 |
| cp7-5 | 1.52 |
| cp7-17 | 3.13 |
| cp7-19 | 5.13 |
| cp7-20 | 5.72 |

According to another exemplary embodiment of the present specification, the first electron transporting material and the second electron transporting material each have a molecular weight of 400 Da to 900 Da.

According to an exemplary embodiment, the first electron transporting material and the second electron transporting material may be used at a volume ratio of 1:99 to 99:1 in the electron transporting layer.

According to an exemplary embodiment, the first electron transporting material and the second electron transporting material may be used at a volume ratio of 1:9 to 9:1 in the electron transporting layer. For example, the first electron transporting material and the second electron transporting material may be used at a volume ratio of 1:9, 2:8, 3:7, 4:6, 5:5, 6:4, 7:3, 8:2, or 9:1 in the electron transporting layer.

According to an exemplary embodiment, the first electron transporting material and the second electron transporting material may be used at a volume ratio of 1:9 to 5:5 in the electron transporting layer.

The second electron transporting material according to an exemplary embodiment of the present specification is relatively better in electron injection and/or electron transporting characteristics than the first electron transporting material. However, even though the electron injection and electron transporting characteristics are excellent, when a balance between holes and electrons is achieved, that is, the ratio of electrons and holes approaches 1, the production of excitons may be increased, thereby maximizing efficiency characteristics of the element.

Accordingly, in order to maximize the production of excitons, it is required to adjust the amount of electrons transferred to the light emitting layer, and the amount of electrons may be adjusted by adjusting the ratio of the first electron transporting material and the second electron transporting material as described above. Accordingly, when the volume ratio of the first electron transporting material and the second electron transporting material according to an exemplary embodiment of the present specification is achieved, it is possible to expect high light emitting efficiency of the element by appropriately adjusting the amount of electrons transferred from the electron transporting layer to the light emitting layer.

According to another exemplary embodiment of the present specification, the organic electroluminescence device further includes an electron injection layer provided between the electron transporting layer and the cathode.

The organic electroluminescence device of the present specification may further include one or more organic material layers between the anode and the light emitting layer.

The organic electroluminescence device of the present specification may further include one or more organic material layers between the light emitting layer and the electron transporting layer and/or the electron transporting layer and the cathode.

For example, the organic electroluminescence device of the present specification may have a structure including a hole injection layer, a hole transporting layer, a light emitting layer, an electron transporting layer, an electron injection layer, and the like as organic material layers. However, the structure of the organic electroluminescence device is not limited thereto, and may include a fewer number of organic layers. FIG. 1 illustrates an example, but the structure of the organic electroluminescence device is not limited thereto, and the organic electroluminescence device of the present specification may also include a fewer number of organic layers, and may further include an additional organic layer.

In another exemplary embodiment, the organic electroluminescence device may be an organic electroluminescence device having a normal type structure in which an anode, an organic material layer, and a cathode are sequentially stacked on a substrate.

In still another exemplary embodiment, the organic electroluminescence device may be an organic electroluminescence device having an inverted type structure in which a cathode, one or more organic material layers, and an anode are sequentially stacked on a substrate.

The organic electroluminescence device of the present specification may be manufactured by materials and methods known in the art, except that an electron transporting layer among the organic material layers includes the first electron transporting material and the second electron transporting material as described above. The electron transporting layer may also include an additional compound in addition to the two materials.

For example, the organic electroluminescence device of the present specification may be manufactured by sequentially stacking a first electrode, an organic material layer, and a second electrode on a substrate. In this case, the organic electroluminescence device may be manufactured by depositing a metal or a metal oxide having conductivity, or an alloy thereof on a substrate to form an anode by using a physical vapor deposition (PVD) method such as sputtering or e-beam evaporation, forming an organic material layer including a hole injection layer, a hole transporting layer, a light emitting layer, and an electron transporting layer thereon, and then depositing a material, which may be used as a cathode, thereon. In addition to the method described above, an organic electroluminescence device may be made by sequentially depositing a cathode material, an organic material layer, and an anode material on a substrate.

When an organic electroluminescence device is manufactured, an organic material layer may be formed by not only a vacuum deposition method, but also a solution application method. Here, the solution application method means spin coating, dip coating, doctor blading, inkjet printing, screen printing, a spray method, roll coating, and the like, but is not limited thereto.

In an exemplary embodiment of the present specification, the first electrode is a cathode, and the second electrode is an anode.

In an exemplary embodiment of the present specification, the first electrode is an anode, and the second electrode is a cathode.

The substrate may be selected in consideration of optical properties and physical properties, if necessary. For example, it is preferred that the substrate is transparent. For the substrate, a hard material may also be used, but the substrate may also be formed of a flexible material such as plastic.

Examples of a material for the substrate include polyethyleneterephthalate (PET), polyethylene naphthalate (PEN), polypropylene (PP), polyimide (PI), polycarbonate (PC), polystyrene (PS), polyoxymethylene (POM), an AS resin (acrylonitrile styrene copolymer), an ABS resin (acrylonitrile butadiene styrene copolymer), triacetyl cellulose (TAC), polyacrylate (PAR), and the like in addition to glass and a quartz substrate, but are not limited thereto.

As the cathode material, a material having a small work function is usually preferred so as to smoothly inject electrons into an organic material layer. Specific examples of the cathode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, but are not limited thereto.

As the anode material, a material having a large work function is usually preferred so as to smoothly inject holes into an organic material layer. Specific examples of the anode material which may be used in the present specification include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly[3,4-(ethylene-1,2-dioxy)thiophene] (PEDOT), polypyrrole, and polyaniline, and the like, but are not limited thereto.

The hole transporting layer is a layer which receives holes from the hole injection layer and transports the holes to the light emitting layer, and a hole transporting material is a material which may receive holes from an anode or a hole injection layer to transfer the holes to a light emitting layer, and is suitably a material having large mobility for the holes. Specific examples thereof include an arylamine-based organic material, an electrically conductive polymer, a block copolymer in which a conjugate portion and a non-conjugate portion are present together, and the like, but are not limited thereto.

The hole injection layer is a layer which injects holes from an electrode, and a hole injection material is preferably a compound which has a capability of transporting holes, and thus has an effect of injecting holes at an anode and an excellent effect of injecting holes for the light emitting layer or the light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is between the work function of the anode material and the HOMO of a peripheral organic material layer. Specific examples of the hole injection material include metal porphyrin, oligothiophene, an arylamine-based organic material, a phthalocyanine derivative, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The light emitting material is a material which may receive holes and electrons from a hole transporting layer and an electron transporting layer, respectively, and combine the holes and the electrons to emit light in a visible ray region, and is preferably a material having good quantum efficiency to fluorescence or phosphorescence. Specific examples thereof include: an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The light emitting material is a material which may receive holes and electrons from a hole transporting layer and an electron transporting layer, respectively, and combine the holes and the electrons to emit light in a visible ray region, and is preferably a material having good quantum efficiency to fluorescence or phosphorescence. Specific examples thereof include: an 8-hydroxy-quinoline aluminum complex (Alq$_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The light emitting layer may include a host material and a dopant material. Examples of the host material include a condensed aromatic ring derivative, or a hetero ring-containing compound, and the like. Specifically, examples of the condensed aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a condensed aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to the hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone and derivatives thereof, a metal complex compound, a nitrogen-containing 5-membered ring derivative, and the like, but are not limited thereto.

EXAMPLE

Hereinafter, the present invention will be described in more detail through the Examples. However, the following Examples are only to exemplify the present invention, but not to limit the scope of the present invention.

Comparative Examples 1-1 to 1-7

A transparent electrode (indium tin oxide) was deposited to a thickness of 100 nm as a hole injection electrode on a glass substrate, and an oxygen plasma treatment was performed at 80 w under a pressure of 30 mtorr for 30 seconds. Heat was added thereon at a vacuum state, thereby depositing [cp1] to a thickness of 30 nm. [cp2] was deposited to a thickness of 800 nm as a hole injection and transporting layer thereon. [cp3] was deposited to a thickness of 200 nm as a hole transporting layer thereon. [cp4] was deposited to a thickness of 20 nm as a light emitting layer thereon, and [cp5] was doped as a light emitting dopant as a volume ratio of 4% thereon. Subsequently, [cp6-1], [cp6-2], [cp6-3], [cp6-4], [cp6-5], [cp6-13], or [cp6-22], which belongs to Formula 1, was deposited to a thickness of 30 nm as an electron transporting and injection layer thereon, LiF was deposited to a thickness of 1 nm as an electron injection layer thereon, and aluminum (Al) was deposited to a thickness of 150 nm as an electron injection electrode thereon, thereby manufacturing an organic electroluminescence device.

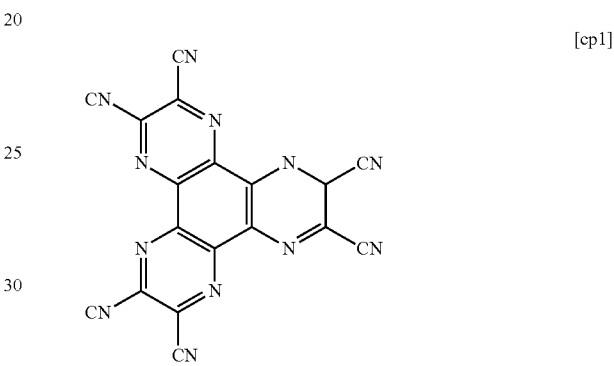

[cp1]

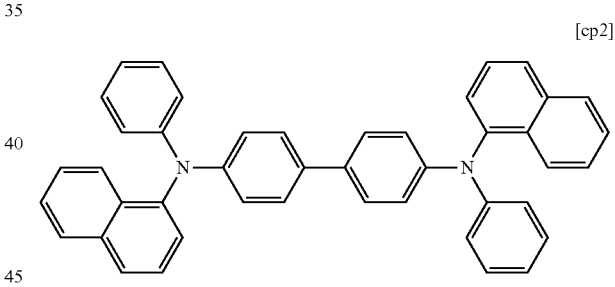

[cp2]

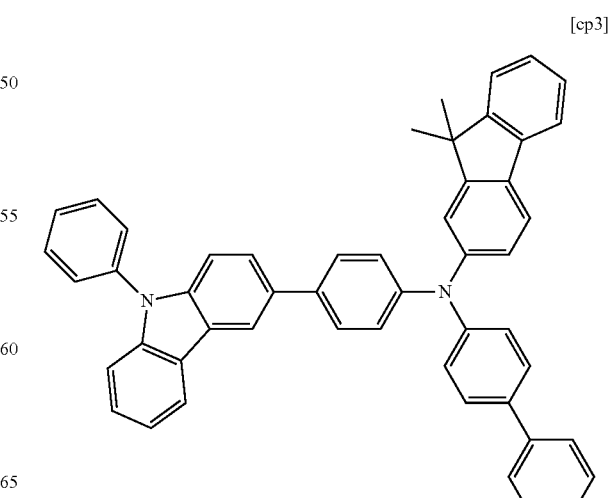

[cp3]

-continued

[cp4]

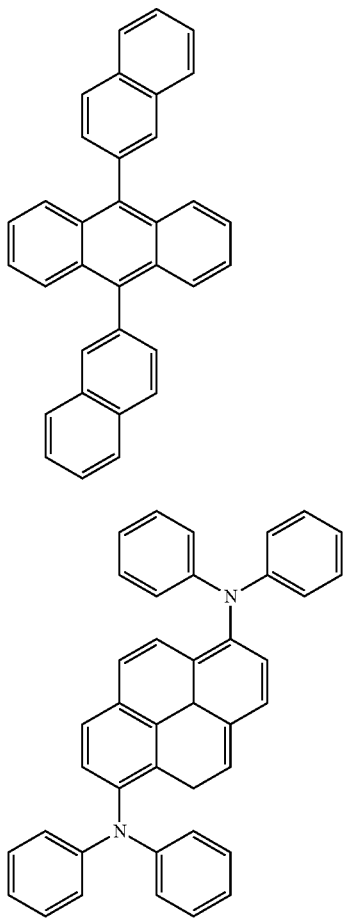

[cp5]

In the aforementioned elements in Comparative Examples 1-1 to 1-7, the voltage and efficiency characteristics at a current density of 10 mA/cm² and the 95% service lives at a brightness of 1,000 nit are shown in the following Table 2.

TABLE 2

| | Formula | V | Cd/A | Service life (hour) |
|---|---|---|---|---|
| Comparative Example 1-1 | Cp6-1 | 5.93 | 4.13 | 2 |
| Comparative Example 1-2 | Cp6-2 | 4.86 | 4.02 | 13 |
| Comparative Example 1-3 | Cp6-3 | 5.12 | 3.79 | 21 |
| Comparative Example 1-4 | Cp6-4 | 5.64 | 3.8 | 25 |
| Comparative Example 1-5 | Cp6-5 | 5.26 | 4.2 | 3 |
| Comparative Example 1-6 | Cp6-13 | 5.38 | 4.01 | 32 |
| Comparative Example 1-7 | Cp6-22 | 5.59 | 3.38 | 28 |

Comparative Examples 2-1 to 2-6

An organic electroluminescence device was manufactured in the same manner as in Comparative Example 1-1, except that [cp7-1], [cp7-2], [cp7-3], [cp7-4], [cp7-5], or [cp7-19] was used as in the following Table 3 instead of the material included in the electron transporting and electron injection layer used in Comparative Example 1-1.

In the aforementioned elements in Comparative Examples 2-1 to 2-6, the voltage and efficiency characteristics at a current density of 10 mA/cm² and the 95% service lives at a brightness of 1,000 nit are shown in the following Table 3.

TABLE 3

| | Formula | V | Cd/A | Service life |
|---|---|---|---|---|
| Comparative Example 2-1 | Cp7-1 | 3.6 | 4.2 | 30 |
| Comparative Example 2-2 | Cp7-2 | 3.7 | 4.3 | 9 |
| Comparative Example 2-3 | Cp7-3 | 3.9 | 3.9 | 4.2 |
| Comparative Example 2-4 | Cp7-4 | 3.7 | 5.39 | 1.2 |
| Comparative Example 2-5 | Cp7-5 | 4.0 | 3.9 | 8.4 |
| Comparative Example 2-6 | Cp7-19 | 3.6 | 4.6 | 7.3 |

Examples 1-1 to 1-27

An organic electroluminescence device was manufactured in the same manner as in Comparative Example 1-1, except that a layer was formed by using one of [cp6-1] to [cp6-5], [cp6-13], and [cp6-22] and one of [cp7-1] to [cp7-5] and [cp7-19] at a volume ratio of 50:50 as in the following Table 4 instead of the material included in the electron transporting and electron injection layer used in Comparative Example 1-1.

In the aforementioned elements in Examples 1-1 to 1-27, the voltage and efficiency characteristics at a current density of 10 mA/cm² and the 95% service lives at a brightness of 1,000 nit are shown in the following Table 4.

TABLE 4

| | Formula | V | Cd/A | Service life |
|---|---|---|---|---|
| Example 1-1 | Cp6-1 & cp7-1 | 3.6 | 4.9 | 40 |
| Example 1-2 | Cp6-1 & cp7-2 | 3.8 | 4.8 | 15 |
| Example 1-3 | Cp6-1 & cp7-3 | 3.6 | 4.95 | 28 |
| Example 1-4 | Cp6-1 & cp7-4 | 3.74 | 5.56 | 14 |
| Example 1-5 | Cp6-1 & cp7-5 | 4.0 | 4.5 | 23 |
| Example 1-6 | Cp6-2 & cp7-1 | 3.9 | 4.1 | 87 |
| Example 1-7 | Cp6-2 & cp7-2 | 4.0 | 3.9 | 45 |
| Example 1-8 | Cp6-2 & cp7-3 | 3.9 | 4.4 | 66 |
| Example 1-9 | Cp6-2 & cp7-4 | 4.1 | 4.0 | 67 |
| Example 1-10 | Cp6-2 & cp7-5 | 4.1 | 4.2 | 51 |
| Example 1-11 | Cp6-3 & cp7-1 | 4.04 | 3.9 | 105 |
| Example 1-12 | Cp6-3 & cp7-2 | 4.2 | 3.7 | 47 |
| Example 1-13 | Cp6-3 & cp7-3 | 4.2 | 4.1 | 82 |
| Example 1-14 | Cp6-3 & cp7-4 | 4.2 | 4.0 | 70 |
| Example 1-15 | Cp6-3 & cp7-5 | 4.1 | 3.9 | 45 |
| Example 1-16 | Cp6-4 & cp7-1 | 3.8 | 4.5 | 63 |
| Example 1-17 | Cp6-4 & cp7-2 | 3.9 | 4.3 | 37 |
| Example 1-18 | Cp6-4 & cp7-3 | 4.0 | 4.3 | 42 |
| Example 1-19 | Cp6-4 & cp7-4 | 3.9 | 4.6 | 33 |
| Example 1-20 | Cp6-4 & cp7-5 | 4.1 | 4.2 | 47 |
| Example 1-21 | Cp6-5 & cp7-1 | 4.0 | 4.6 | 56 |
| Example 1-22 | Cp6-5 & cp7-2 | 4.2 | 4.4 | 28 |
| Example 1-23 | Cp6-5 & cp7-3 | 4.1 | 4.5 | 35 |
| Example 1-24 | Cp6-5 & cp7-4 | 4.3 | 4.2 | 21 |

TABLE 4-continued

|  | Formula | V | Cd/A | Service life |
|---|---|---|---|---|
| Example 1-25 | Cp6-5 & cp7-5 | 4.4 | 3.9 | 22 |
| Example 1-26 | Cp6-22 & cp7-19 | 4.0 | 4.6 | 62 |
| Example 1-27 | Cp6-13 & cp7-19 | 4.4 | 4.2 | 82 |

When the results of Tables 2 to 4 are compared with each other, it can be confirmed that in the case of the organic electroluminescence device including the electron transporting layer according to an exemplary embodiment of the present specification as in Examples 1-1 to 1-27, it is possible to implement an organic electroluminescence device having a low driving voltage, high efficiency, and a long service life as compared to the organic electroluminescence device including the electron transporting layer including one organic material as in Comparative Examples 1-1 to 1-7 and Comparative Examples 2-1 to 2-6.

Comparative Examples 3-1 to 3-4

An organic electroluminescence device was manufactured in the same manner as in Comparative Example 1-1, except that a layer was formed by using one of the following [Compound A-1] and [Compound A-2] and one of [Compound B-1] to [Compound B-3] at a volume ratio of 50:50 as in the following Table 6 instead of the material included in the electron transporting and electron injection layer used in Comparative Example 1-1.

[Compound A-1]

[Compound A-2]

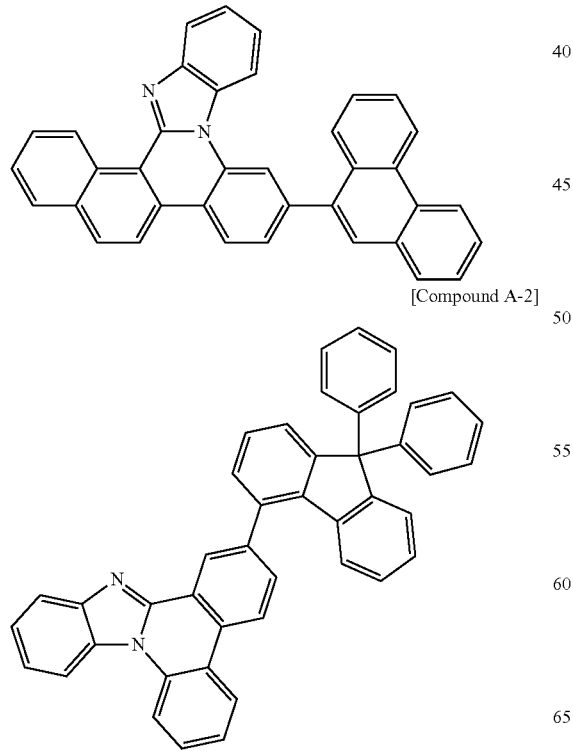

[Compound B-1]

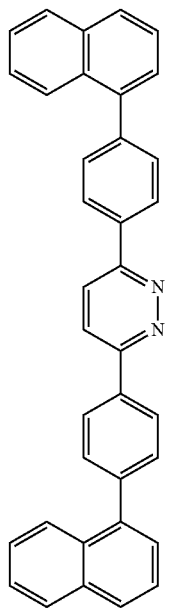

[Compound B-2]

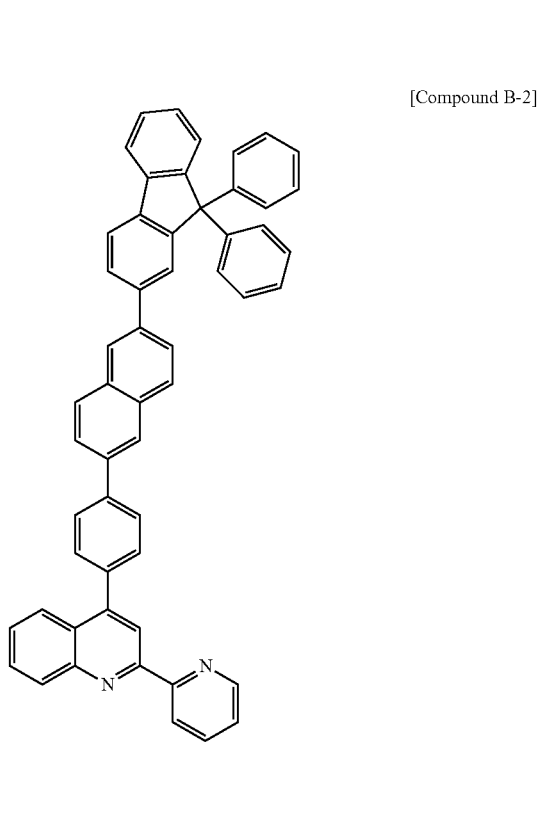

-continued

[Compound B-3]

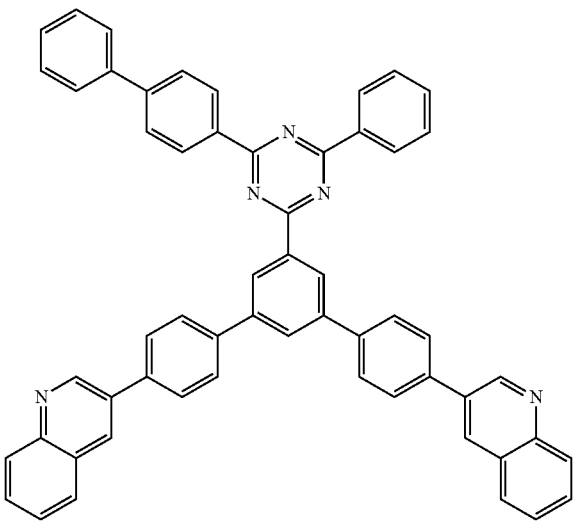

The values of the dipole moments of Compounds A-1, A-2, and B-1 to B-3 are shown in the following Table 5.

TABLE 5

| Compound | Dipole moment |
| --- | --- |
| A-1 | 2.70 |
| A-2 | 2.63 |
| B-1 | 3.31 |
| B-2 | 3.80 |
| B-3 | 4.58 |

In the aforementioned elements in Comparative Examples 3-1 to 3-4, the voltage and efficiency characteristics at a current density of 10 mA/cm$^2$ and the 95% service lives at a brightness of 1,000 nit are shown in the following Table 6.

TABLE 6

| | Formula | V | Cd/A | Service life |
| --- | --- | --- | --- | --- |
| Comparative Example 3-1 | Compound A-1 & Compound B-1 | 5.0 | 4.0 | 16 |
| Comparative Example 3-2 | Compound A-1 & Compound B-2 | 5.1 | 3.9 | 17 |
| Comparative Example 3-3 | Compound A-2 & Compound B-1 | 5.3 | 4.2 | 15 |
| Comparative Example 3-4 | Compound A-2 & Compound B-3 | 5.5 | 4.1 | 20 |

When the results of Table 6 are observed, it can be confirmed that when the dipole moment values of Compounds B-1 to B-3 corresponding to the first electron transporting material including an N-containing six-membered ring are larger than those of Compounds A-1 and A-2 corresponding to the second electron transporting material including a five-membered hetero ring which includes at least one heteroatom of N, O, and S as in Comparative Examples 3-1 to 3-4, a driving voltage is high, light emitting efficiency is low, and service life characteristics deteriorates as compared to the Examples described in Table 4 of the present invention. The aforementioned results were obtained because when the dipole moment value of the second electron transporting material is smaller than the dipole moment value of the first electron transporting material, the ability of the electron transporting layer including the first and second electron transporting materials to inject electrons deteriorates, thereby requiring a high driving voltage.

Accordingly, as in an exemplary embodiment of the present specification, when the dipole moment value of the second electron transporting material including a five-membered hetero ring which includes at least one heteroatom of N, O, and S, or a cyano group is larger than the dipole moment value of the first electron transporting material including a monocyclic or polycyclic ring which includes an N-containing six-membered ring, the ability of the electron transporting layer including the first electron transporting material and the second electron transporting material to inject and transport electrons is improved, so that it is possible to expect a low driving voltage and high efficiency.

Comparative Examples 4-1 to 4-4

An organic electroluminescence device was manufactured in the same manner as in Comparative Example 1-1, except that a two-layered electron transporting layer was stacked by depositing one compound of [cp6-1], [cp6-4], [cp7-2], and [cp7-5] to a thickness of 20 nm, and then depositing the other compound of [cp6-1], [cp6-4], [cp7-2], and [cp7-5] to a thickness of 10 nm as in the following Table 7, instead of the material included in the electron transporting and electron injection layer used in Comparative Example 1-1.

In the aforementioned elements in Comparative Examples 4-1 to 4-4, the voltage and efficiency characteristics at a current density of 10 mA/cm$^2$ and the 95% service lives at a brightness of 1,000 nit are shown in the following Table 7.

TABLE 7

| | Formula | V | Cd/A | Service life |
| --- | --- | --- | --- | --- |
| Comparative Example 4-1 | Cp6-1 (20 nm)/cp7-2 (10 nm) | 4.4 | 4.2 | 12 |
| Comparative Example 4-2 | Cp6-4 (20 nm)/cp7-4 (10 nm) | 4.4 | 3.9 | 16 |
| Comparative Example 4-3 | Cp7-2 (20 nm)/cp6-1 (10 nm) | 6.2 | 2.9 | 6 |
| Comparative Example 4-4 | Cp7-5 (20 nm)/cp6-4 (10 nm) | 5.9 | 3.1 | 5 |

When the results of Table 7 are observed, it can be confirmed that when a first electron transporting material and a second electron transporting material are used in mixture in an one-layered electron transporting layer according to an exemplary embodiment of the present specification, it is possible to provide an element having a low driving voltage, high light emitting efficiency, and a long service life as compared to the case where a two-layer stacked electron transporting layer is used by using the two electron transporting materials.

The invention claimed is:
1. An organic electroluminescence device comprising:
an anode;
a cathode;
a light emitting layer provided between the anode and the cathode; and
an electron transporting layer provided between the cathode and the light emitting layer,
wherein the electron transporting layer comprises a first electron transporting material and a second electron transporting material, the first electron transporting material is an organic material comprising a monocyclic or polycyclic ring which includes an N-containing six-membered ring, the second electron transporting material is an organic material comprising a five-membered hetero ring which includes at least one heteroatom of N, O, and S, or a cyano group, and a dipole moment of the second electron transporting material is larger than a dipole moment of the first electron transporting material.

2. The organic electroluminescence device of claim 1, wherein the first electron transporting material has a dipole moment of 0 Debye to 3 Debye, and the second electron transporting material has a dipole moment of 1 Debye to 7 Debye.

3. The organic electroluminescence device of claim 1, wherein the first electron transporting material comprises a structure represented by the following Formula 1:

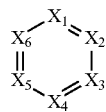

[Formula 1]

in the Formula 1, one to three of $X_1$ to $X_6$ is (are) N, the others are $CR_1$ and $R_1$ is a monovalent organic group, and adjacent monovalent organic groups optionally combine with each other to form a substituted or unsubstituted aliphatic ring or a substituted or unsubstituted aromatic ring.

4. The organic electroluminescence device of claim 1, wherein the first electron transporting material is an organic material comprising pyridine, pyrimidine, or triazine.

5. The organic electroluminescence device of claim 1, wherein the second electron transporting material comprises a structure represented by the following Formula 5:

[Formula 5]

in the Formula 5, $Y_1$ is $NR_{21}$, O, or S, $Y_2$ to $Y_5$ are the same as or different from each other, and are each N or $CR_{22}$, $R_{21}$ and $R_{22}$ are the same as or different from each other, and are each a monovalent organic group, and adjacent monovalent organic groups optionally combine with each other to form a substituted or unsubstituted aliphatic ring or a substituted or unsubstituted aromatic ring.

6. The organic electroluminescence device of claim 1, wherein the second electron transporting material is an organic material comprising imidazole, oxazole, or thiazole.

7. The organic electroluminescence device of claim 1, wherein the second electron transporting material is an organic material comprising benzimidazole, benzoxazole, or benzothiazole.

8. The organic electroluminescence device of claim 1, wherein the second electron transporting material comprises a structure represented by the following Formula 14:

$$CN\text{-}(L_{31})_t\text{-}R_{31}$$ [Formula 14]

in Formula 14, $L_{31}$ is a divalent organic group and t is an integer of 0 to 4, and when t is 2 or more, $L_{31}$'s are the same as or different from each other, and $R_{31}$ is a monovalent organic group.

9. The organic electroluminescence device of claim 1, wherein the first electron transporting material and the second electron transporting material do not comprise a metal element or a metal complex.

10. The organic electroluminescence device of claim 1, wherein the first electron transporting material and the second electron transporting material do not comprise a metal complex.

11. The organic electroluminescence device of claim 1, wherein the first electron transporting material and the second electron transporting material each have a molecular weight of 400 Da to 900 Da.

12. The organic electroluminescence device of claim 1, wherein the electron transporting layer comprising the first electron transporting material and the second electron transporting material comprises the first electron transporting material and the second electron transporting material at a volume ratio of 1:99 to 99:1.

13. The organic electroluminescence device of claim 1, further comprising:

an electron injection layer provided between the electron transporting layer and the cathode.

* * * * *